US008848868B2

(12) United States Patent  
Davydov et al.

(10) Patent No.: US 8,848,868 B2  
(45) Date of Patent: Sep. 30, 2014

(54) X-RAY SYSTEM AND METHOD OF USING THEREOF

(75) Inventors: Albert Davydov, Forest Hills, NY (US); Peter Usov, Belle Mead, NJ (US)

(73) Assignee: Albert Davydov, Forest Hills, NY (US)

( * ) Notice: Subject to any disclaimer, the term of this patent is extended or adjusted under 35 U.S.C. 154(b) by 280 days.

(21) Appl. No.: 13/547,256

(22) Filed: Jul. 12, 2012

(65) Prior Publication Data
US 2013/0051523 A1 Feb. 28, 2013

Related U.S. Application Data

(60) Provisional application No. 61/526,726, filed on Aug. 24, 2011, provisional application No. 61/588,274, filed on Jan. 19, 2012.

(51) Int. Cl.
*A61B 6/00* (2006.01)
*A61B 5/107* (2006.01)
*A61B 5/0402* (2006.01)

(52) U.S. Cl.
CPC .......... *A61B 6/505* (2013.01); *A61B 6/547* (2013.01); *A61B 6/588* (2013.01); *A61B 6/542* (2013.01); *A61B 6/563* (2013.01); *A61B 6/582* (2013.01); *A61B 5/1071* (2013.01); *A61B 6/5211* (2013.01); *A61B 5/0402* (2013.01)
USPC .......................................................... 378/62

(58) Field of Classification Search
CPC ...... A61B 6/0306; A61B 6/582; A61B 6/504; A61B 6/505; A61B 5/0402; A61B 6/482; G01N 23/04

USPC ........................................... 378/4, 19, 62, 207
See application file for complete search history.

(56) References Cited

U.S. PATENT DOCUMENTS

| 7,976,568 | B2* | 7/2011 | Cheung et al. ............... 606/279 |
| 2001/0028697 | A1* | 10/2001 | Nahaliel et al. ................ 378/19 |
| 2003/0215122 | A1* | 11/2003 | Tanaka .......................... 382/128 |
| 2007/0167741 | A1 | 7/2007 | Sherman et al. |
| 2008/0183071 | A1 | 7/2008 | Strommer et al. |
| 2008/0199060 | A1* | 8/2008 | Boyden et al. ................ 382/131 |
| 2009/0209852 | A1 | 8/2009 | Mate et al. |
| 2011/0157230 | A1 | 6/2011 | Davydov |

FOREIGN PATENT DOCUMENTS

EP 1788948 B1 6/2011

* cited by examiner

*Primary Examiner* — Irakli Kiknadze
(74) *Attorney, Agent, or Firm* — Anna Vishev

(57) ABSTRACT

An X-ray system including an X-ray source generating X-rays, an X-ray receptor receiving the X-rays and generating X-ray images, a patient satellite and a server connected to the X-ray source, the X-ray receptor and the patient satellite. The patient satellite is secured to a patient positioned between the X-ray source and the X-ray receptor and includes an angular orientation sensor and a distance sensor. The angular orientation sensor detects an angular orientation of the patient and outputs a signal to an operator allowing the operator to position the patient with respect to the X-ray source and the X-ray receptor so as to eliminate an angular distortion in the X-ray images. The distance sensor measures a distance between the patient and the X-ray receptor.

16 Claims, 3 Drawing Sheets

X-RAY SYSTEM AND METHOD OF USING THEREOF

RELATED APPLICATION

This application claims all rights of priority to U.S. Provisional Patent Application No. 61/526,726 filed on Aug. 24, 2011 and U.S. Provisional Patent Application No. 61/588,274 filed on Jan. 19, 2012, which are fully incorporated herein by reference.

BACKGROUND

This application and its disclosure generally relate to the field of taking X-ray images, in particular, the images of a person's spine using X-ray technology.

Various kinds of illnesses can be traced to deformations in the spines of patients. In order to obtain a prognosis for such illnesses, for many years standard practice has been to obtain images of the spines of patients and the visually inspect these images and review the patients' medical histories. Typically, deformations of the spine can be a result of a congenital condition, or can result from a severe trauma suffered during an automotive accident, a fall, a physical altercation, etc. It is a directive of the American Medical Association (AMA) that an evaluator must assess spinal segments for abnormal motion during a routine evaluation of spine. In addition, the AMA publishes data mandating a specific protocol of quantification and ranges of such evaluation. Unfortunately, until now there was very little practice of quantitative analysis from such images due to technical difficulties and distortions during X-ray taking procedures, as also noted by the AMA. Therefore a physician had to rely on anecdotal evidence and his years of experience to make a reasonably accurate prognosis, or quantifications. X-rays have been used for more than a hundred years for generating images showing human anatomical structures, e.g., the components of the spinal column. However, since existing systems for this purpose have many disadvantages in generating accurate X-rays for purposes of generating intelligible quantification reports from the X-rays images, it became a time consuming and erroneous process subjected to a number of human errors making the end result, i.e., the quantification report, highly inaccurate.

In an earlier application by the present inventor (i.e., U.S. patent application Ser. No. 12/881,411) an X-ray system is disclosed for capturing X-ray images of a portion of a patient's spine, the images including an L-shaped target of known dimensions which is attached to the patient's body. The X-rays are produced with the image of the target and analyzed using the image of the target as scaling indicator and a process is discussed for automatically, or semi-automatically analyzing the X-ray images and generating quantification data that assists a doctor in establishing of a diagnosis and a prognosis of the patient.

While the system described in the earlier application works well and provides a great improvement in the state of the art, it still has some shortcomings. One of them is that it is specific only to the newer X-ray systems (such as the ones made by GE) and may not work for others older systems. A further disadvantage is that it does not address reliably the problems associated with errors and uncertainties associated with magnitude of systems generators which generate variations of intensities of energy produced, and therefore making the target non-visible in the image created.

SUMMARY

In one general aspect, the present invention is an X-ray system including an X-ray source generating X-ray's, an X-ray receptor receiving the X-rays and generating X-ray images, a patient satellite and a server connected to the X-ray source. The patient satellite is secured to a patient positioned between the X-ray source and the X-ray receptor and includes an angular orientation sensor, X-ray radiation sensor and a distance sensor. The angular orientation sensor detects an angular orientation of the patient relative to the direction of X-rays (for proper performance, this orientation must be close to 90 degrees) and outputs a signal to an operator allowing the operator to position the patient with respect to the X-ray source at a correct angle so as to eliminate an angular distortion on the X-ray receptor of the X-ray images. The distance sensor measures a distance between the patient and the X-ray receptor for magnification adjustment purposes. The X-ray radiation (or diode) sensor is utilized for the purposes of quantifying and documenting a cumulative X-ray dose for the human body for the purposes of documentation which will be included in the quantification radiology reports, and also for dose monitoring purposes of X-ray generators. It is this inventor's observation and further conclusion based on significant number of testing of different X-ray equipment that, not only different generators output different amounts of X-Ray radiation, but also the same generator may output different doses during the same kind of X-ray procedure depending on various factors like temperature of the X-ray head, electricity load, age of the X-ray unit, etc. It has been observed on a number of X-ray units registered in New York City that with a "cold" X-ray head the equipment may emit a lesser dose of radiation than a dose emitted after a few of the same kinds of X-rays has been taken. These outputs vary significantly and this phenomenon poses significant public health risk since X-rays are invasive and their effect is latent and cumulative. Further, it is this inventor's observation that different equipment generators within the same model category of the same manufacturer during same type of exposures may output different X-ray radiation doses. In the present invention, the X-ray radiation/diode sensor records all cumulative doses during X-ray procedures for the purposes of keeping the record for patient's and provider's safety, further analysis and control of the dose.

In another general aspect, the present invention is a method of taking X-ray images. The method includes providing an X-ray source generating X-rays and providing an X-ray receptor receiving the X-rays and generating X-ray images. The method also includes securing a patient satellite to a patient positioned between the X-ray source and the X-ray receptor, the patient satellite including an angular orientation sensor, X-ray radiation sensor or diode measuring the X-ray intensity and a distance sensor for magnification/scaling factor adjustments, detecting an angular orientation of the patient using the angular orientation sensor, and outputting a signal to an operator allowing the operator to position the patient with respect to the X-ray source and the X-ray receptor so as to eliminate an angular distortion in the X-ray images. The distance sensor measures a distance between the patient and the X-ray receptor, and the X-ray source and the X-ray receptor. Knowing the exact distances the scaling factor is mathematically calculated using simple mathematical calculations. In accordance with the invention, a server is provided and connected to the X-ray source, the X-ray receptor and the patient satellite via a microprocessor and a bluetooth connection, the X-ray images being transmitted from the X-ray receptor to the server via a known process called parsing.

The above aspects, advantages and features are of representative embodiments only. It should be understood that they are not to be considered limitations on the invention as defined by the claims. Additional features and advantages of the invention will become apparent in the following description, from the drawings, and from the claims.

BRIEF DESCRIPTION OF THE DRAWINGS

The invention is illustrated by way of examples which are not a limitation, and the figures of the accompanying drawings in which references denote corresponding parts, and in which.

DETAILED DESCRIPTION OF THE PREFERRED EMBODIMENT AND THE DRAWINGS

Figure 1:
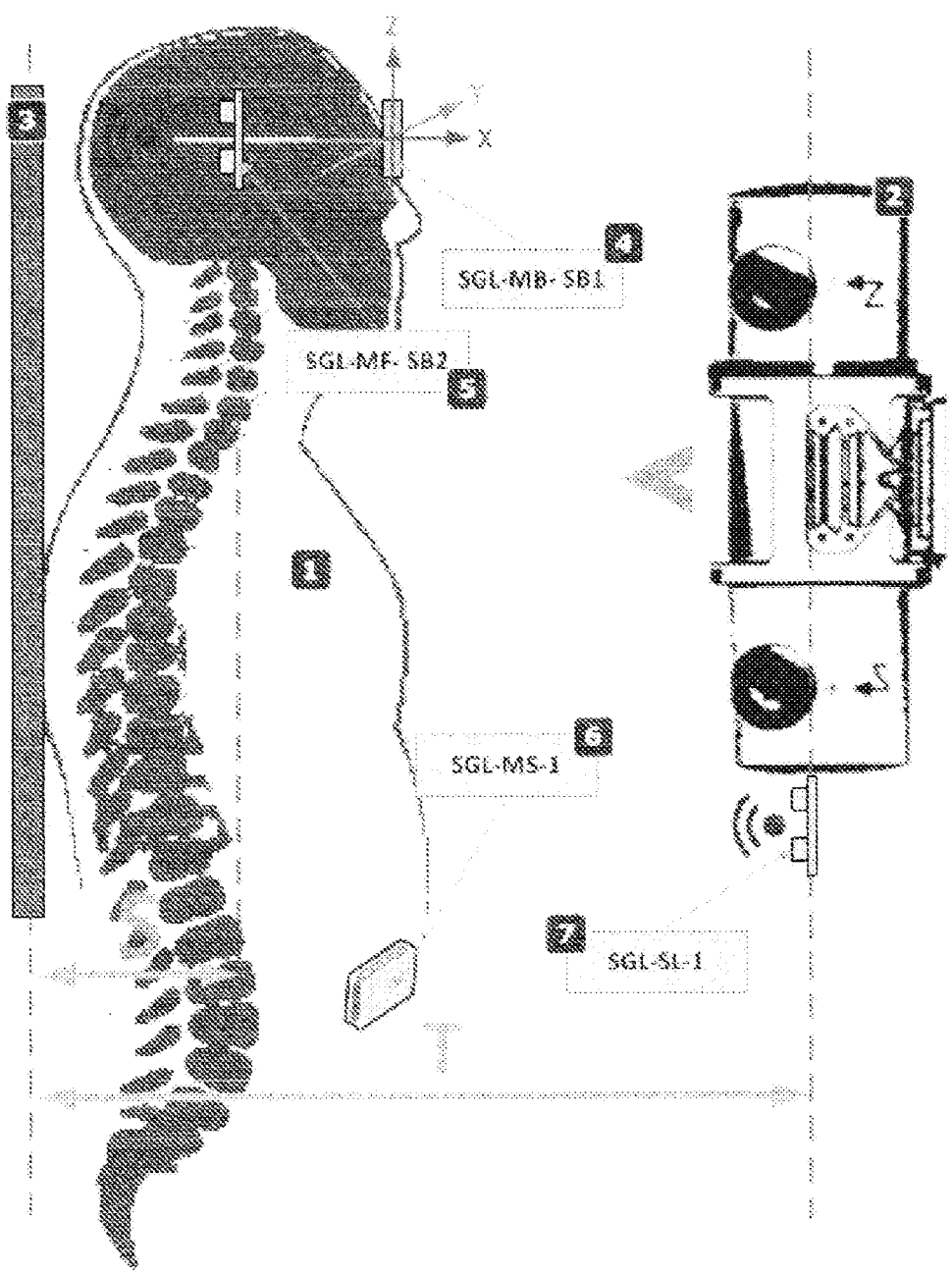
FIG. 1 is a schematic diagram of the preferred embodiment of the invention showing preferred locations and positioning of the sensors in the frontal positioning of the patient.

The spine consists of a series of vertebrae and interconnecting tissues disposed and arranged along the length of the skeleton mammals. In humans, the cord assumes several curvatures and is partitioned along these curvatures into four regions, cervical, thoracic, lumbar, and lumbar-sacral. The vertebrae of the different regions (and sometimes, even within the same region), have different shapes and sizes.

Damage caused either by sudden impact to the spine either vertically along its axis or laterally, congenital defects, or certain diseases can cause the vertebrae to deform or even portions thereof to break off, causing discomfort or pain to the patient, and impairing his ability to bend and move his body. Moreover, lateral translational (rather than rotational) traumatic forces between adjacent vertebrae may cause the internal channels of adjacent vertebrae to be offset to the point where the spinal cord passing therethrough can be damaged, or even severed, resulting in major health problems to the patient, such as loss of the ability to move or sense the body part/s.

As described in the inventor's patent application Ser. No. 12/881,411, incorporated herein by reference, dimensions and relative positions of the various vertebrae with respect to each other can be determined utilizing plain X-ray images. This information is then available as a means of assessing the condition of a patient.

More specifically, the shape and position of the vertebrae are determined from X-ray images. Once each vertebra is identified on an image, and processed within the device, the automated software that is a part of a device is used to mathematically analyze the spine or at least a region thereof, and, using this analysis, to generate a diagnosis for the patient. A problem plaguing this analysis until now has been that each vertebrae is specific to the size of the patient and images taken have magnification and orientation distortions occurring because of the relative positions of the X-ray beam source, the patient and the X-ray image recorder (film), and as a result, the exact shape, size and position relative to another vertebra is difficult to determine accurately for quantification purposes from conventional X-ray images Obviously, any errors in determining the shape, orientation and size of a vertebra may result in an erroneous diagnosis, treatment and a prognosis of a disease.

A further problem in detecting the shape, size and position of vertebrae exactly is that the spinal vertebra and the actual shape of the whole spine can look quite different and can change from person to person based on a large number of factors such as age, sex, injuries and pathological changes in the vertebra and the spine itself.

Another problem is that the existing systems, like DX Analyzer which does not solve the distortion problems due to magnification and orientation. Although an operator is preselecting the source of X-rays and film distance, it does not specify the position of the patient in relation to the source of X-rays and the film. If the patient is standing closer to the X-ray source the image on the film will appear larger than actual, and if the patient is standing closer to the film, the image will appear closer to the actual size. Moreover, if he does not stand completely straight and/or not facing in a direction that is exactly perpendicular to the direction of the X-ray beam, the orientation (angular optical) distortion of an X-ray image becomes an issue since the 2 axial geometry of a shadow of the 3 axial vertebra is changing when the vertebra is relocated relative to the three axial space. Because of these flaws the accuracy of measurements is not attainable with the method used by the DX Analyzer.

In the related U.S. patent application Ser. No. 12/881,411, incorporated herein by reference, the inventor described the use of a digital compass to accurately position the person with respect to the X-Ray source. After conducting empirical studies, the inventor discovered that while it was easy to position the body exactly "aligned along axis Y-Y perpendicularly to axis X-X" using only the digital compass, the lead plate used in the related application to correct for magnification distortion did not always appear at the resulting image. It was later discovered that the image of the lead plate depends significantly on the intensity of the X-ray machine. This intensity varies greatly from one machine to another, as well as within machines themselves due to the factors affecting the generators during normal use.

To eliminate the above problems and in accordance with the preferred embodiment, a novel system is presented for taking X-rays which functions with any X-ray equipment. The present system utilizes sensors which control 3-dimensional distortions during an X-ray image taking procedure and assist in adjustment of any angular distortion which was registered during taking of the X-ray image. Once the information is recorded during the X-ray taking procedure the information is transferred to the server system via Bluetooth electronic board or any other suitable wireless connection.

Figure 2:
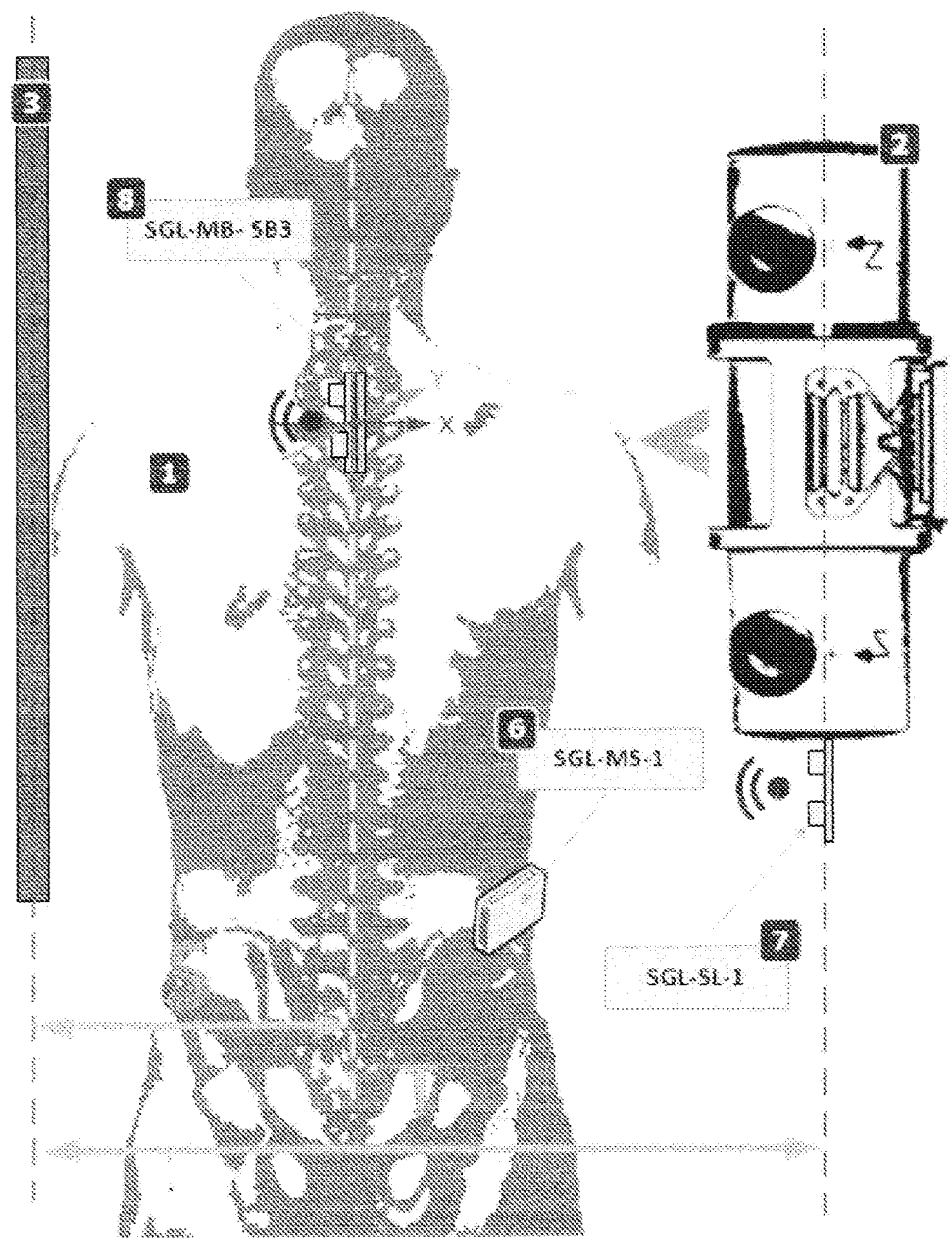
FIG. 2 is a schematic diagram of the preferred embodiment of the invention showing preferred locations and positioning of the sensors in the lateral positioning of the patient.

As shown in FIGS. 1 and 2, the system includes an X-ray source 2 generating X-rays directed at a patient 1. The X-rays pass through the patient and are intercepted by a receptor. The receptor is used to generate a raw image. While there are many different kinds of receptors on the market, in one embodiment an x-ray sensor array 3 is used. Such arrays are available from GE, Naomi, and other well-known sources.

In the preferred embodiment, the locator sensors system includes two wirelessly accessible sets of sensors: a primary set of sensors; and a secondary set of sensors. FIGS. 1 and 2 show preferred locations and positioning of the sensors. The primary set of sensors preferably includes a main board device 6; a frontal radiation sensor module 4 measuring effective skin input radiation dose in x-ray examinations for the frontal view; a distance sensor module 5 measuring distance S, i.e., the distance from the distance sensor module 5 to the X-Ray sensor array 3; and a lateral radiation sensor module 8 measuring effective skin input radiation dose in x-ray examinations for the lateral view. In the preferred embodiment, distance sensor module 5 is connected to the frontal radiation sensor module 4 via a cable. The frontal radiation sensor module 4 is, in turn, connected to the main board device 6 via a cable. The primary set of sensors and the angular orientation sensor (including the digital compass) are connected together into a patient satellite 10. Patient satellite 10 also preferably includes a Bluetooth transceiver for communicating with the local server as described below.

The secondary set of sensors preferably includes a main board device (not shown) and a second distance sensor module 7 measuring distance T, i.e., the distance between the X-Ray source 2 and X-Ray sensor array 3. The main board device and the second distance sensor module 7 are preferably formed in a unitary housing as an X-Ray source satellite 12.

Figure 3:
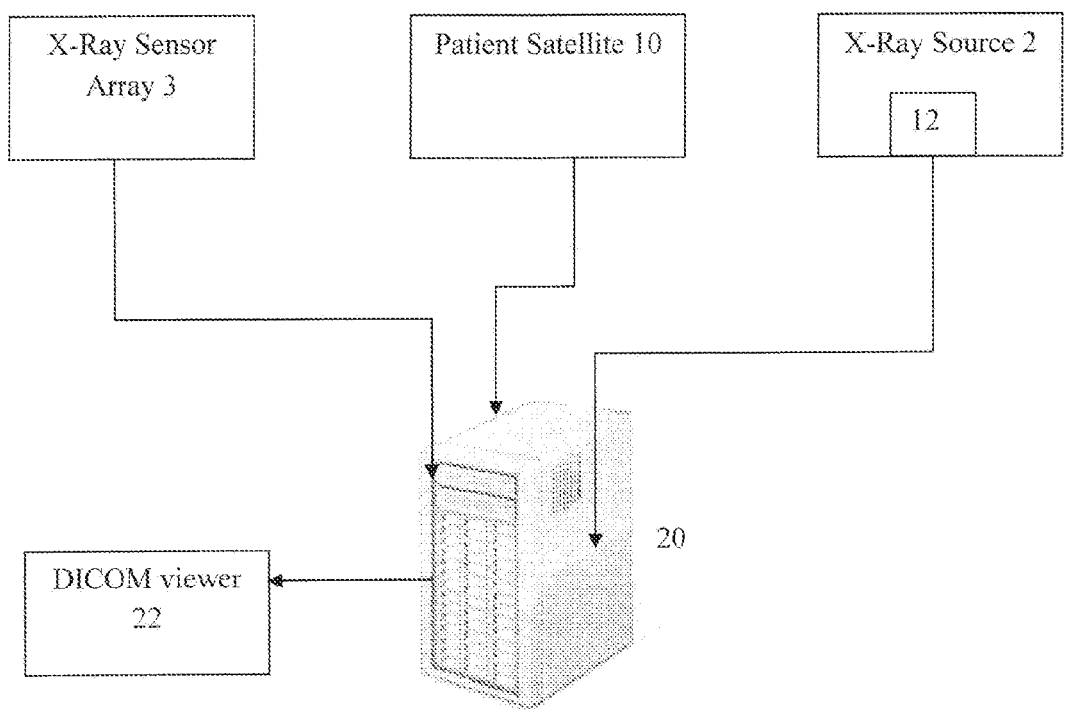
FIG. 3 is a schematic diagram of the X-ray system.

The system further includes a local server 20 (shown in FIG. 3). The X-ray source satellite 12 and the patient satellite 10 are in communication with the local server via a conventional wireless communication channel, such as Bluetooth. Moreover, as schematically shown in FIG. 3, raw images collected by the X-ray sensor array 3 are also sent to the local server.

Preferably, the patient satellite is small enough (less than about 1"×1") and is light-weight, preferably less than 100 grams. If necessary, the above-described components and others can be provided in two or more cases. The satellite is attached to the patient, at a convenient location closest to a respective body part to be imaged.

In one embodiment, a single ECG electrode-type pad is attached to the skin of the patient using an adhesive and a button which is attached to the patient's satellite. The satellite is then snapped to the ECG electrode by means of the button.

The system operates as follows. First, the patient's satellite is calibrated toward the X-ray tube of the X-ray system, so that the positioning of the satellite would be at the third axis at zero degrees enabling correction for the third axis to produce a pure lateral X-ray view without the 3rd axial interferences. The calibration angles are saved in the system. The patient receives the patient satellite component, which is then attached to the ECG electrode by means of the button. The patient is then positioned between the source of the X-rays and the sensor array.

The angular positioning of patient's parts is adjusted as required for a particular kind of X-ray image utilizing the 3-axial angular sensor by moving the patient to a specific positioning guided by the angular sensor to provide a pure lateral view. The angular positioning of the patient is monitored by the angular sensor. The sensor provides an indication to a technician as to its position. In one embodiment, the indication is dynamic (and is visual and/or audible) to assist the technician in positioning the patient to a predetermined angular orientation. Thus, the angles can be defined in three dimensions.

Once the patient is positioned properly, the X-ray source is turned on, and it starts generating X-rays. They pass through the patient and the patient's satellite and reach the X-ray sensor array. When the X-rays are sensed by the X-ray sensor in the patient satellite, the data from the angular sensor and the ultrasound sensors is saved and a message is sent to the local server to connect to the X-ray sensor array and detect the X-ray image (parsing).

The images are studied in a DICOM viewer 22 connected to the local server 20. The DICOM viewer displays the received X-ray images with all of the corrections (as described in this specification) allowing a radiologist to place proper markings on the images. Once the image markings are finished by the radiologist, they are saved at the local server, and the coordinates of the markings from the DICOM viewer are sent to a remote location for quantifications and a report (preferably in a PDF format) is produced with specific X-ray intensities which were registered by the X-ray radiation sensor.

In one embodiment, when the X-ray image is received by the local server 20, the image is processed and several corrections are made. One correction is a magnification correction that takes into consideration the distances between the X-ray source, the patient and the X-ray sensor array. In order to correct a magnification error, the value of the magnification is calculated for each particular instance of taking X-ray images. The value of the magnification M is calculated using the following formula $$M = \frac{T}{T-S},$$

where T is the distance between the X-ray source and the sensor array, as measured by the second distance sensor module 7, and S is the distance between the patient and the sensor array, as measured by the distance sensor module 5. Knowing the value of the magnification, each image can be uniformly adjusted.

Another correction takes into consideration, angular offsets of the various visual elements in the x-ray image.

Finally, a correction for an X-ray exposure may also be necessary. It is this inventor research conclusion that the variations in X-ray exposures produced by the same X-ray unit depend on the temperature of the X-ray beam. Once the X-ray system's output is monitored an unnecessary X-ray exposure to the patient can be avoided by constantly monitoring performances of the X-ray unit. As soon as the intensity of the X-ray beam is not consistent proper machine and image adjustment can be made and the inconsistency noticed in the report.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. An X-ray system comprising:
    an X-ray source generating X-rays;
    an X-ray receptor receiving the X-rays and generating X-ray images;
    a patient satellite secured to a patient positioned between the X-ray source and the X-ray receptor, the patient satellite including an angular orientation sensor detecting an angular orientation of the patient and outputting a signal to an operator allowing the operator to position the patient with respect to the X-ray source and the X-ray receptor so as to eliminate an angular distortion in the X-ray images, the patient satellite further including a distance sensor measuring a distance between the patient and the X-ray receptor; and
    a server connected to the X-ray source, the X-ray receptor and the patient satellite, the server receiving the X-ray images from the X-ray receptor.

2. The X-ray system of claim 1, wherein the patient satellite further comprises an X-ray radiation sensor measuring an X-ray exposure received by the patient.

3. The X-ray system of claim 1 further comprising an X-ray source satellite secured to the X-ray source, wherein the X-ray source satellite includes a second distance sensor measuring a distance between the X-ray source and the X-ray receptor.

4. The X-ray system of claim 3 wherein the measurements of the distance sensor and the second distance sensor are transmitted to the server and wherein the server adjusts the X-ray images received from the X-ray receptor for magnification error by calculating an actual magnification for each of the received X-ray images.

5. The X-ray system of claim 4, wherein said actual magnification M is calculated using a formula $$M = \frac{T}{T-S},$$

wherein T is the distance between the X-ray source and the X-ray receptor, as measured by the second distance sensor, and wherein S is the distance between the patient and the X-ray receptor, as measured by the distance sensor.

6. The X-ray system of claim 5, wherein said server comprises a DICOM viewer displaying said X-ray images, said images being free from said angular distortion and being corrected for a magnification distortion using said actual magnification M.

7. The X-ray system of claim 1, wherein said signal outputted to an operator is a visual signal.

8. The X-ray system of claim 1, wherein said signal outputted to an operator is an audible signal.

9. The method of claim 1, wherein said signal outputted to an operator is a visual signal.

10. The method of claim 1, wherein said signal outputted to an operator is an audible signal.

11. A method of taking X-ray images, the method comprising the steps of:
   providing an X-ray source generating X-rays;
   providing an X-ray receptor receiving the X-rays and generating X-ray images;
   securing a patient satellite to a patient positioned between the X-ray source and the X-ray receptor, the patient satellite including an angular orientation sensor and a distance sensor;
   detecting an angular orientation of the patient using the angular orientation sensor and outputting a signal to an operator allowing the operator to position the patient with respect to the X-ray source and the X-ray receptor so as to eliminate an angular distortion in the X-ray images;
   using the distance sensor to measure a distance between the patient and the X-ray receptor;
   providing a server connected to the X-ray source, the X-ray receptor and the patient satellite; and
   transmitting the X-ray images from the X-ray receptor to the server.

12. The method of claim 11, further comprising a step of measuring an X-ray exposure by the patient using an X-ray radiation sensor and producing a report including the measured X-ray exposure.

13. The method of claim 12 further comprising steps of
   securing an X-ray source satellite to the X-ray source, the X-ray source satellite including a second distance sensor; and
   measuring a distance between the X-ray source and the X-ray receptor using the second distance sensor.

14. The method of claim 13 further comprising steps of
   transmitting the measurements of the distance sensor and the second distance sensor to the server; and
   using the server to adjust the X-ray images received from the X-ray receptor for magnification error by calculating an actual magnification for each of the received X-ray images.

15. The method of claim 14, wherein said actual magnification M is calculated using a formula $$M = \frac{T}{T-S},$$

wherein T is the distance between the X-ray source and the X-ray receptor, as measured by the second distance sensor, and wherein S is the distance between the patient and the X-ray receptor, as measured by the distance sensor.

16. The method of claim 15, further comprising a step of displaying said X-ray images on a DICOM viewer, said images being free from said angular distortion and being corrected for a magnification distortion using said actual magnification M.

* * * * *